United States Patent [19]
Sager et al.

[11] Patent Number: 5,162,225
[45] Date of Patent: Nov. 10, 1992

[54] GROWTH OF CELLS IN HOLLOW FIBERS IN AN AGITATED VESSEL

[75] Inventors: Bill C. Sager, Midland, Mich.; Melvin Rothberg, Plantation, Fla.; Roger B. Hornby, Sanford, Mich.; Jeffrey D. Michalowski, Midland, Mich.; David J. Forgach, Midland, Mich.; Gordon E. Fleig, Oakland, Calif.

[73] Assignee: The Dow Chemical Company, Midland, Mich.

[21] Appl. No.: 729,663

[22] Filed: Jul. 15, 1991

Related U.S. Application Data

[63] Continuation-in-part of Ser. No. 325,262, Mar. 17, 1989, abandoned, and a continuation-in-part of Ser. No. 579,920, Sep. 7, 1990, abandoned.

[51] Int. Cl.$^5$ .......................... C12N 5/00; C12N 5/02
[52] U.S. Cl. ...................... 435/240.243; 435/240.2; 435/240.23; 435/240.241; 435/240.242; 435/240.25; 435/240.27
[58] Field of Search ...................... 435/240.1, 240.246, 435/240.27, 240.25

[56] References Cited

U.S. PATENT DOCUMENTS

| | | |
|---|---|---|
| 3,821,087 | 6/1974 | Knazek et al. |
| 3,883,393 | 5/1975 | Knazek et al. |
| 3,997,396 | 12/1976 | Delente |
| 4,087,327 | 5/1978 | Feder et al. |
| 4,184,922 | 1/1980 | Knazek et al. |
| 4,266,032 | 5/1981 | Miller et al. |
| 4,442,206 | 4/1984 | Michaels et al. |
| 4,495,288 | 1/1985 | Jarvis, Jr. et al. |
| 4,546,083 | 10/1985 | Meyers et al. |
| 4,647,539 | 3/1987 | Bach |
| 4,757,017 | 7/1988 | Cheung |
| 4,863,856 | 9/1989 | Dean, Jr. et al. |
| 4,994,388 | 2/1991 | Hillegas et al. |

FOREIGN PATENT DOCUMENTS

| | | |
|---|---|---|
| 0150288A2 | 8/1985 | European Pat. Off. |
| 0183184 | 6/1986 | European Pat. Off. |
| 0205997A2 | 12/1986 | European Pat. Off. |
| 2013370 | 6/1988 | Japan |
| 2016972 | 7/1988 | Japan |
| 63-196271 | 8/1988 | Japan |
| 63-196272 | 8/1988 | Japan |
| 63-196274 | 8/1988 | Japan |
| 63-196275 | 8/1988 | Japan |
| 63-196277 | 8/1988 | Japan |
| 63-196278 | 8/1988 | Japan |
| 63-196279 | 8/1988 | Japan |
| 63-196281 | 8/1988 | Japan |
| 63-196282 | 8/1988 | Japan |
| 63-196283 | 8/1988 | Japan |
| 63-196284 | 8/1988 | Japan |
| 63-196285 | 8/1988 | Japan |
| 63-196286 | 8/1988 | Japan |
| 63-196287 | 8/1988 | Japan |
| 63-198280 | 8/1988 | Japan |
| 63-198975 | 8/1988 | Japan |
| 63-198976 | 8/1988 | Japan |
| 63-198977 | 8/1988 | Japan |
| 63-198978 | 8/1988 | Japan |
| 63-198979 | 8/1988 | Japan |
| 63-198980 | 8/1988 | Japan |
| 63-198981 | 8/1988 | Japan |
| 02013370 | 1/1990 | Japan |
| 1491261 | 5/1975 | United Kingdom |
| 2178447A | 2/1987 | United Kingdom |
| 8602378 | 4/1986 | World Int. Prop. O. |

OTHER PUBLICATIONS

Kang et al. (May 1990) Annals of the New York Academy of Sciences, vol. 589, pp. 192–202.
Shukla et al. (1989) Applied Biochemistry and Biotechnology, vol. 20/21, pp. 571–586.
Klebe et al. (1981) Journal of Cellular Physiology 190: 481–488.
Kang et al., "Novel Membrane-Based Immobilization Technique for Bioreactors", *Conference on Biochemical Engineering*, Santa Barbara, Oct. 2–7, 1988.
R. Shukla et al., "Novel Hollow Fiber Immobilization Techniques for Whole Cells and Advanced Bioreactors", *Appl. Biochem. Biotechnol*, 20/21, pp. 571–586 (1989).
W. K. Kang et al., "Novel Membrane-Based Immobilization Technique for Bioreactors", *Ann. N. Y. Acad. Sci.*, 589, pp. 192–202 (1990).
K. Ku et al., "Development of a Hollow-Fiber System for Large-Scale Culture of Mammalian Cells", *Biotechnol. Bioeng.*, 23, 79–95 (1981).
M. Hirtenstein et al., "Microcarriers for Animal Cell Culture: A Brief Review of Theory and Practice", *Develop. Biol. Standard*, 46, 109–116 (1979).
S. Reuveny et al., "Apparatus and Methodology for Microcarrier Cell Culture", *Adv. Appl. Microbiol.*, 31, pp. 139–179 (1986).
S. R. Adamson et al., "Industrial Mammalian Cell Culture", *Canadian J. Chem. Eng.*, 64, 531–539 (Aug. 1986).
W. Hu et al., "Cultivation of Mammalian Cells in Bioreactors", *Biotechnol. Prog.*, 1, pp. 209–215 (1985).
Z. Bohak et al., "Novel Anchorage Matrices for Sus-
(List continued on next page.)

*Primary Examiner*—David L. Lacey
*Assistant Examiner*—Gian P. Wang

[57] ABSTRACT

Hollow fiber structures for culturing mammalian cells in an agitated media are disclosed. These hollow fibers have a cylindrical wall surrounding a lumen preferably open at opposite ends of the fiber and have a length along the axis parallel to the lumen of not more than 5 centimeters. Hollow fiber structures which have their exterior surface coated to prevent cell attachment and growth thereon are also disclosed.

25 Claims, No Drawings

OTHER PUBLICATIONS pension Culture of Mammalian Cells", *Biopolymers*, 26, S205–S213 (1987).

Adema et al., "Use of Porous Microcarriers in Agitated Cultures", *BioPharm,* Jul./Aug. 1990, pp. 20–24.

R. J. Klebe et al., "Adhesive Substrates for Fibronectin", *J. Cell Phys.,* 109, pp. 481–488 (1981).

E. Ruoslahti et al., "Arg-Gly-Asp A Versatile Cell Recognition Signal", *Cell,* 44, 517–518 (1986).

M. D. Pierschbacher et al., "Variants of the Cell Recognition Site of Fibronectin That Retain Attachment-Promoting Activity", *Proc. Natl. Acad. Sci.,* USA 81, pp. 5985–5988 (1984).

Adhesion Peptides in ECM Connections (Winter 1990), a quarterly newsletter by Telios Pharmaceuticals, Inc., winter 1990.

Derwent Publication, 87-280390, Japanese Kokai J6 2163-688-A, Mar. 26, 1986.

GROWTH OF CELLS IN HOLLOW FIBERS IN AN AGITATED VESSEL

CROSS-REFERENCE TO RELATED APPLICATION

This application is a continuation-in-part of our co-pending application Ser. No. 07/325,262 filed Mar. 17, 1989, now abandoned and our co-pending application Ser. No. 07/579,090 filed Sep. 7, 1990, now abandoned.

BACKGROUND OF THE INVENTION

The present invention relates to the culturing of mammalian cell types and more particularly to the use of novel structures for culturing mammalian cells in submerged culture.

It is a common procedure to use various single cells microorganisms, such as yeast and bacteria, in a liquid-nutrient medium for the production of various fermentation products. More recently there has been an an increase in the exploitation of hybridoma, animal, plant, insect and genetically engineered mammalian cells to obtain pharmacologically and diagnostically useful products. The use of mammalian cells to produce pharmaceutical and diagnostic valuable products has resulted in efforts to culture mammalian cells on a large scale.

As mammalian cells are more fragile than microorganisms, they must be grown under conditions which avoid the shear forces associated with turbulence encountered in the well developed technology of industrial microbiology for culturing microorganisms. To avoid excessive shear forces during cell growth, mammalian cells, and particularly anchorage dependent cells (ADC), have traditionally been grown on a large scale on the inside walls of rotating bottles. In such instances, growth of relatively thin layers of cells on the inside surface of these bottles represents only a small fraction of the bottle volume. To increase the cell density within a reactor vessel, hollow fiber reactors, consisting of a bundle of hollow fibers surrounded by a shell, have been used for growing various mammalian cells. See, for example, U.S. Pat. Nos. 3,883,393; 3,997,396; and 4,804,628.

A major limitation of hollow fiber culture devices is that as the cells grow and the cell density increases, it becomes more difficult for the nutrients, oxygen, and other chemical stimuli in the growth medium to diffuse through the walls of the hollow fiber membranes and through the layers of cells that have developed to reach remote cells (cells which are furthest away from the reactor membranes). It also becomes equally difficult for waste material produced by the remote cells to diffuse back into the lumen of the hollow fiber membranes. Other limitations include fiber leaks, poor accessibility to the extracapillary spaces, an undesirable pressure drop across the device as it is scaled up, and the fibers sticking together reducing the surface area to which the cells may attach.

To overcome the limitations inherent in the previous systems, cells have been attached to various carrier systems. Solid microcarriers fabricated from glass, silica, polystyrene, cross-linked dextran or polyhydroxyethylmethacrylate have been used for the cultivation of cells. See, for example, M. Kiremitci et al., *Enzyme Microb. Technol.* 11, 205–224 (1989): S. Reuveny, *Adv. Biotechnol. Proc.* 2, 1–32 (1980). Polystryene resin beads derivatized with amino acids, peptides, or hydroxy carboxylic acids and their use in culturing cells is described in U.S Pat. No. 4,266,032. British Patent 2,178,447 describes fiber networks or open pore foams having open areas or pores in which cells can be grown. However, as mammalian cells attach and grow on the outer surfaces of a microcarrier system, it is still necessary to avoid excessive shear forces encountered at mixing rates necessary to promote adequate nutrient and oxygen transfer in large scale reactors.

Another disadvantage of using various carrier systems for mammalian cells, and particularly ADC, is the inoculum size required. This is of particular importance as cells will attach to the outer surfaces of the carrier as well as within the pores and internal structures when the cells are incubated with the carrier at low mixing speeds. The cells attached to the outside surface will often be destroyed by high shear forces when agitation is increased to promote adequate nutrient and oxygen transfer.

It would therefore be desirable to provide simple protective structures in which mammalian cells can be grown. Structures having uniform dimensions which promote consistent cell growth but which can be fabricated at low cost are particularly desirable. In addition, for large scale production of products by mammalian cells it would be desirable to reduce the number of cells and manipulative steps necessary for inoculation.

SUMMARY OF THE INVENTION

The present invention is directed to a method of culturing mammalian cells which attach to a surface comprising (a) providing a plurality of essentially individual hollow fiber segments in a vessel, the segments each having an exterior surface and an interior surface, wherein each fiber segment comprises a cylindrical wall surrounding a lumen open at at least one end of the fiber, the lumen diameter being in the range from about 50 to about 1000 microns, and the lumen of the hollow fiber segments being characterized as being compatible with retention, growth and propagation of mammalian cells, and the length of the fiber along the axis parallel to the lumen being not more than about 5 centimeters:

(b) introducing into the vessel a liquid nutrient medium:

(c) introducing into the vessel a cell culture in the presence of the liquid nutrient medium: and (d) agitating the nutrient medium to distribute the hollow fibers in the medium: and (e) maintaining conditions in the liquid medium so that the cell culture will propagate in the lumens of the hollow fiber segments.

In another aspect of the invention, the exterior surfaces of the hollow fiber segments are characterized as substantially preventing attachment and growth of mammalian cells thereon.

In still another aspect of the invention, the interior surfaces of the hollow fiber segments are coated with a material which promotes the adhesion of mammalian cells to the hollow fiber segment.

DETAILED DESCRIPTION OF THE INVENTION

The term "cell" or "cells" as used hereinafter, refers to the culturing of mammalian cells unless specified otherwise. The term "culturing of cells" is used herein to refer to growth, propagation, production of products from cells, and/or biotransformation by cells.

The present invention is directed to novel relatively short hollow fibers in which cells can be cultured in the fiber lumen.

The hollow fibers of the present invention are used in relatively short fiber segment form. In general, the length of these fibers along the axis parallel to the lumen of the fiber will be in the range from about 2 to about 1000 times the diameter of the lumen, more preferably about 5 to about 250 times the diameter of the lumen, most preferably about 5 to about 50 times the diameter of the lumen.

The length of these hollow fibers is preferably in the range from about 0.01 centimeter to about 5 centimeters, more preferably about 0.02 centimeter to about 3 centimeters and most preferably about 0.05 to about 1 centimeter. Fibers which are prone to become entangled are preferably cut to lengths less than about 2 centimeters long, more preferably shorter than about 1 centimeter. The optimum length of the fiber segment will depend upon the cell type and the composition of the fiber used. For example, if a fiber has walls permeable to nutrients and metabolic waste products but not permeable to the desired cell products is too long, then the desired cell products will have to be transported along and through the length of the fiber lumen to the open end or ends and the resulting concentration of cell products may adversely affect the cells. If the fiber segments are too long they may also become entangled reducing nutrient and oxygen exchange. On the other hand, if the fiber is too short, the volume contained within the lumen in which cells may grow undisturbed by nutrient agitation is relatively small for each fiber. One of ordinary skill in the art can readily determine the optimum length for the fiber based upon the cell type, product desired and fiber composition.

The diameter of the lumen of the fiber may be varied depending upon the optimum conditions for growing a specific cell line within the fiber. In general, it is desirable that the diameter of the lumen be at least about two times the mean dimension of a cell to be cultured in the direction perpendicular to the surface on which the particular cell line resides but not greater than about 30 times this mean cell dimension. Preferably, the lumen diameter for the fiber is such that it can contain a layer of about 2 to about 20 cells. In a preferred embodiment, the lumen diameter is at least about 50 microns, more preferably at least about 100 microns and most preferably at least about 150 microns. In a preferred embodiment, the lumen diameter is preferably less than about 1000 microns, more preferably less than about 800 microns and most preferably less than about 600 microns. For fibers with walls not permeable to desired cell products, the preferred lumen diameter may be larger than for fibers having permeable walls so as to facilitate transport of products out of the lumen. Dimensions of the fiber are conveniently determined by microscopic analysis.

The wall thickness of the hollow fiber is advantageously great enough that the fiber retains mechanical strength and integrity in the environment in which cells are cultured. If nutrients or waste products are to pass through the porous wall of the fiber, the wall should have sufficient porosity and not be so thick that transport of nutrients or metabolic waste products through the walls of the fiber to or from the cells within the lumen is greatly impeded. In order for nutrients and cell products to readily pass through the walls of the fiber, the porosity and effective pore size must be appropriately selected. In general, the wall thickness of the fiber in the nutrient medium is preferably in the range from about 5 to about 100 microns. More preferably, the wall thickness of the fiber in the medium is in the range from about 10 to about 50 microns.

The walls of the hollow fibers used herein may be porous or non-porous. The term "porous" as used herein means the fibers in the nutrient medium have pores extending through the fiber wall so as to communicate from the lumen surface to the exterior surface with a pore size greater than 0.01 microns in diameter which permits ready passage of nutrients and metabolic waste products through the walls of the fiber. The term "non-porous" as used herein means the fibers in the nutrient medium do not have pores or have pores less than 0.01 microns in diameter extending from the lumen surface to the exterior surface.

A porosity of the fibers in the range from about 10 to about 70 percent is preferred in certain embodiments of the invention. Fibers with high porosities may be used if the fiber retains the desired physical strength properties, but a porosity less than about 80% is generally advantageous. Porosity is conveniently determined from the ratio of the difference of the the density of the material which consitutes the fiber walls minus the apparent density of the fiber wall material divided by the difference between the density of the fiber wall material minus the density of the medium. Some fibers will swell in the nutrient medium and become more permeable, or in effect, more porous.

The mean diameter of pores in the walls of the porous hollow fibers used herein should not be so great as to cause cells to grow within the pores of the fiber walls and thereby potentially damage the fiber or impede transport of nutrients to the lumen of the hollow fiber. Preferably, an effective mean diameter for the pores in the wall should be less than about 2 micron, more preferably less than about 0.5 microns. Pore size of fibers having pores of greater than 0.05 microns mean diameter is conveniently determined by bubble point measurement in accordance with ASTM F-316-70. The effective size of pores having a smaller mean diameter is determined by measuring the molecular weight permeability cut-off of the fiber using molecules of a known size. The pores should be sufficiently large to permit the desired products to pass though the pores but exclude the cells from entering the pore. Some cell products of relatively high molecular weight will require larger pores for egress than lower molecular weight products. Thus, one would employ a pore size to exclude the cells from entering the pore and as large as possible to allow for the rapid permeation of nutrients and products in and out of the lumen.

The hollow fiber is desirably fabricated from a material on which the cells readily attach and grow. Almost any polymer or material used for fabrication of a filtration or ultrafiltration membrane compatible with cell attachment and growth is suitable for fabrication of the hollow fibers used for the present invention. Illustrative materials from which porous and non-porous fibers can be made to which cells readily attach and grow include cellulose acetate and other cellulose esters, polyvinylalcohol, polyamides, polyvinyl chloride, organic silicone polymers, polyacrylonitrile, copolymers of styrene and acrylonitrile, polysulfone, polyethersulfone, polyesters, polycarbonate, polymethylmethacrylate and blends of these polymers with materials compatible with the porous hollow fibers and non-toxic to the cells. A preferred polymers for fabrication of the hollow fibers are cellulose acetate and cellulose triacetate. It may also be desirable in some embodiments of the invention to treat the lumen membrane surface to render it more hydrophilic. For example, certain polymers can be treated by corona discharge, sulfonation or other chemical reactions. West German published Patent (OLS) 3,521,684 describes the coating of polymers with growth factors which may allow a higher concentration of cells to be obtained in the reactor, the disclosure of which is hereby incorporated by reference.

It may also be desirable in some embodiments of the invention to coat at least one of the surfaces of the hollow fiber to alter the tendency of mammalian cells to attach thereon. The term "coat" or "coated" means that the exterior or lumen membrane surface of the hollow fibers are treated with a material which covers the membrane of the hollow fibers but does not destroy the porosity or structural integrity of the fibers. The term "attach" or "attachment" is used herein to refer to the adhesion or sticking of cells to the hollow fiber walls. There are several methods for carrying out this embodiment of the present invention. When hollow fibers are fabricated from a material to which cells readily attach, the exterior surface of the fiber membranes is coated with a material to substantially prevent cell attachment to the exterior fiber surface. When the hollow fibers are fabricated from a material to which cells do not readily attach, the lumen of the fiber can be coated with a material which promotes cell adhesion. The invention also contemplates coating both the exterior and interior surface, the exterior surface to prevent cell attachment, and the lumen surface coated to promote cell adhesion.

The use of fibers coated on the exterior surface to prevent cell attachment obviates the need to produce an excessively large number of cells for use as an inoculum for initiation of growth in large scale operations as a minimal number of cells adhere to the exterior surfaces where they will be damaged or destroyed by shear forces during mixing and movement of nutrients.

In general, the material used to coat the exterior surface of the hollow fibers to prevent cell attachment will have the following characteristics: be non-toxic to mammalian cells if released into the aqueous medium; not otherwise have a deleterious affect on the structural characteristics of the fiber walls such as destroying the porosity or weakening the structural integrity of the fiber; be stable to chemical or heat sterilization processes; and be relatively inexpensive to apply.

Material used to coat the lumen surface of the hollow fibers to promote cell attachment; will in general also be non-toxic to mammalian cells; not otherwise have a deleterious affect on the structural characteristics of the fiber walls such as destroying the porosity or weakening the structural integrity of the fiber; be stable to chemical or heat sterilization processes; be relatively inexpensive to apply; and be capable of interacting with or having an affinity for the hollow fiber material so that it adheres to the inner surface of the hollow fiber.

Advantageously, after coating a surface of the fibers, the fibers do not loose excessive permeability or porosity.

An appropriate means for coating the exterior surface of hollow fibers to prevent cell attachment is to coat the exterior surface with an ethylenically unsaturated carboxylic monomer, i.e., a monomer that will polymerize or copolymerize via vinyl addition polymerization in a manner similar to ethylene. Representative compounds and procedures to coat the exterior surfaces of porous hollow fibers are given in U.S. Pat. No. 4,909,943, the disclosure of which is hereby incorporated by reference. Another means to coat the exterior surface is to coat with an aqueous solution containing a hydrophilic polymer and/or monomer having reactive groups and a catalyst. See, Flemming F. Stengaard, Characteristics and Performance of New Types of Ultrafiltration Membranes with Chemically Modified Surfaces, *Desalination*, 70, 207–224 (1988), the disclosure of which is hereby incorporated by reference. In a preferred embodiment, the exterior of the hollow fibers is coated with a copolymer derived from hydroxyethyl methacrylate and methacrylic acid.

While not wishing to be bound by theory, it is believed that the coatings on which cells do not adhere will provide a highly charged surface which repels the cells rather than allowing for cell attachment. In addition, it is believed that suitable polymers used to treat the fibers selectively plug discontinuities or defects within the fibers without forming an impervious coating, allowing the fibers to retain their porosity or permeability.

Appropriate materials which can be used to treat the lumen membrane surface to enhance cell adhesion include fibronectin [see M. Pierschbacher and E. Ruoslahti, *Proc. Natl. Acad. Sci.* 81, 5985–5988 (1984)]; polylysine, [see R. Klebe et al, *J. Cell. Phys.* 109, 481–488 (1981)]; collagen, [see W. Dessau et al. *Biochem. J.*, 169, 55–59 (1978)]; serum-derived glycoproteins, [see E. Ruoslahti and A. Vaheri, *Biochim. Biophys. Acta* 631, 350–358 (1980)]; gelatin or various adhesion peptides such as those marketed by Telios Pharmaceuticals, Inc.

Coating the lumen surface of a hollow fiber is particularly advantageous when the hollow fiber is fabricated from a material to which cells do not readily attach. Illustrative materials for fabricating porous and non-porous hollow fibers to which most ADC do not readily adhere include polystyrene, polypropylene, polyethylene, polymethylpentene and saponified cellulose esters.

Polymers particularly well suited to use to culture cells are those which are generally employed in the prior art in hollow fiber bioreactors like those described in U.S. Pat. Nos. 3,821,087 and 3,883,393. A polymer found particularly useful for preparation of the coated hollow fibers of this invention is cellulose acetate having a degree of acetylation in the range of about 22 to about 45 percent by weight. Commercial cellulose diacetate (having an acetyl content in the range from about 32 to about 41 weight percent), cellulose triacetate (having an acetyl content in the range from about 41 to about 45 percent) or mixtures thereof are preferred. The hollow fibers described herein can be readily made by techniques known in the prior art. In general, porous cellulose ester hollow fibers are made by melt spinning from a composition containing a compatible solvent and a polyol nonsolvent followed by leaching the polyol solvent mixture from the fiber. Other techniques for producing porous cellulose acetate hollow fibers are described in U.S. Pat. No. 4,276,173, the disclosure of which is hereby incorporated by reference.

Techniques for making non-porous and non-permeable hollow fibers are well known in the prior art, see, for example, Encyclopedia of Polymer Science and Engineering 6, 802-839 (1986). A method for producing non-porous hollow fibers from a spinnable polymer by a melt-spinning or a wet-spinning process is described in U.S. Pat. No. 3,081,490, the disclosure of which is hereby incorporated by reference.

Another example of a process for making hollow fibers known in the prior art is that of making porous polyethylene hollow fibers. U.S. Pat. No. 4,229,297 describes the making of polyethylene hollow fibers by blending the polyethylene with dioctylphthalate and finely divided silica, extruding the mixture through a spinnerette or die and then extracting the silica in a sodium hydroxide solution and extracting the dioctylphthalate in 1,1,1-trichloroethane. Techniques for modifying the porosity and pore size of the fibers by modifying draw ratio, varying percent additives in the polymer during spinning, adjusting the temperature at which spinning, leaching or quenching of the fiber occurs, are known to those skilled in the art.

Once these fibers are spun, optionally drawn, leached where necessary and plasticized, if necessary, the fiber can be coated as herein previously described and subsequently cut or otherwise divided into relatively short segments.

Conveniently, the fiber can be cut into short segments using a microtome or other conventional means for slicing the fiber without closing the lumen thereof. Optionally, a fluid may be present in the lumen of the fiber while it is being cut to keep the lumen open. i.e., keep it from collapsing. It is technically feasible to use a water jet or other non-mechanical means to cut the fiber into short segments so long as precautions are taken to avoid sealing the lumen of the fiber or otherwise adversely affecting the fiber shape so as to limit access to the interior. A laser may also be used to cut the fibers, provided the fiber is not deleteriously affected beyond the cut, e.g., loosing porosity or altering the surface coating. The fiber may also be cut at an angle producing an elliptical instead of circular lumen opening to increase the available surface area for inoculation. The optimum angle for cutting the fibers may be determined by those skilled in the art depending upon the fiber composition and the cells to be cultured.

In general, it is desirable that the fibers be more dense than the nutrient medium as the fibers and attached cells will settle to the bottom of the vessel and can readily be removed from the medium. In some embodiments of the invention, it may be desirable for the fibers to be less dense than the nutrient medium as a means to readily separate the fibers from cells which are not attached to the fibers.

The hollow fiber structures described herein are advantageously used as protective structures for cells in an apparatus for promoting culturing of cells which attach or stick to a surface when cultured in a liquid nutrient medium. Such cells include anchorage dependent mammalian cells and loosely adherent hybridoma cells. Adherent hybidoma cells are hybridoma cells which will attach or stick to a hollow fiber surface. The apparatus comprises a quantity of essentially individual fibers within a vessel which can contain a liquid nutrient medium in which cells can be cultured. By the term "essentially individual hollow fibers", it is meant that the fibers are generally not attached or permanently affixed to one another in a complex structure. Small groups of fibers may become affixed to one another during processing but generally the fibers will be independent and free floating within the vessel containing an agitated and/or stirred liquid nutrient medium. The vessel desirably has appropriate inlets and outlets for introduction of fibers, sterilants, nutrient media, cells to be cultured and desired gases and cell product and spent nutrient removal. Advantageously, the vessel contains controllable means for maintaining the desired temperature in the vessel. Sensors for monitoring pH, temperature and other parameters as may be desirable. The liquid nutrient medium contains the nutrients required by the cell line being cultured for optimum growth as well as oxygen or other gases which may be required. Agitation of the nutrient medium helps to insure that the fibers are generally uniformly distributed in the medium. Agitation also promotes exchange of fresh nutrient medium with metabolic waste material and other products produced by the cells. Agitation of the medium may be achieved by one or more techniques, including sparging of gas, mechanical stirring, pumping a portion of the nutrient medium to circulate it or other conventional techniques. Whatever technique or techniques are used for agitation, it is desirable to promote exchange of the nutrient medium with metabolic waste products of the cells without deleterious impact or shear on the lumen surface of the fibers.

The use of the hollow fibers and coated hollow fibers in the present invention are particularly advantageous for culturing ADC and hybridoma cells at agitation rates where the shear stress produced from the aeration and mixing is sufficiently high to damage or dislodge cells present on the outer surface of a microcarrier. The amount of shear stress sufficient to damage or dislodge cells present on a microcarrier will depend upon the cell type, reactor design, etc. One of ordinary skill in the art can readily determine the amount of shear stress which will damage or dislodge the cells from a microcarrier. For example, the maximum population of chick embryo fibroblasts grown in stirred microcarrier cultures was correlated with an "integrated shear factor" (ISF) obtained by dividing the impeller tip speed by the distance between the impeller tip and the vessel wall. A sharp drop in maximum cell density was reported at an ISF of about 90 s$^{-1}$ for cells allowed to attach to microcarriers for 24 hours before agitating [*Ann. N.Y. Acad. Sci.* 369, 47-59 (1981)]. For FS-4 cells, a sharp drop in relative growth was found to occur at and IFS of 20-25 s$^{-1}$ [*Biotechnol. Bioeng.* 29, 130-141 (1987)]. Similarly the growth of Vero cells on Cytodex I ™ microcarriers in magnetic spinner vessels decreases at 90 rpm or greater [see, Hirtenstein and Clark, in *Tissue Culture in Medical Research,* Richards and Rajan, Eds. (Pergamon Oxford, England, 1980) p.97.

The optimum temperature, nutrient medium composition, rate of agitation of the liquid nutrient medium and other parameters for culturing cells will depend upon the cell line being cultured, the size and length of the hollow fibers, the stage of the culturing and other factors. One of ordinary skill in the art can readily determine the optimum rate of agitation, the composition of the nutrient medium, the temperature of the medium and other factors to obtain maximum cell growth and product production. For example, see F. Dhainaut et al., *J. Biotechnol.* 5, 131-138 (1987): T. Y. Tao et al., *J. Biotechnol.* 6, 205-224 (1987). Also, for example, when mammalian cells are propagated, a narrow temperature range of from about 35° C.-40° C. is typically employed: whereas, for example, if the cells are reptilian in origin, lower or higher temperatures may be employed.

Examples of mammalian cell lines which can be cultured in the hollow fiber structures and apparatus described hereinbefore include: Chinese hamster ovary (CHO); human embryo lung, such as MRC-5 and MRC-9; primary cells such as human and bovine anterior pituitary cells; African green monkey kidney cells, such as VERO and BSC-1; human cervix carcinoma cells (Hela); Syrian hamster AV12 cells, etc. These cells may optionally be genetically modified to produce specific products of interest. The cell products may be retained within the cell or may accumulate in the nutrient medium. Products excreted into the medium can be readily concentrated or recovered by conventional techniques, such as affinity chromatography or ultrafiltration. If the product is retained within the cells, the cells can be recovered from the carriers, cells lysed, and products concentrated and purified by conventional techniques. Purification of cell products can be accomplished by other techniques known in the art.

The cells can be introduced into the fibers by placing the fibers in a medium containing cells and permitting migration of cells into the fiber lumen. Alternatively the lumen may be inoculated directly by passing inoculum down the lumens of the fibers and then cutting the fibers. In one embodiment, fibers are introduced into the liquid nutrient medium, allowed to equilibrate, cells are then added and the cells and fibers mixed by gently agitating the system. Fibers can be made more wettable by introducing a carbon dioxide atmosphere into the fiber and then displacing the gas with nutrient medium. Because carbon dioxide affects the pH of the medium, cells are advantageously not present during this wetting step.

Advantageously, the fibers are sterile or essentially free of organisms other than the desired cell line. Generally fibers which are not heat stable are sterilized prior to their introduction into the vessel. Ethylene oxide, gamma radiation or other conventional sterilization techniques may be used. Fibers can also be sterilized in the vessel in which cells are to be cultured. For example, fibers which are not deleteriously affected by elevated temperatures can be directly sterilized in the vessel in which cells are to be cultured using autoclave conditions. Periodically, when the cell culture line no longer produces the desired cell product at an acceptable rate, it may be desirable to remove the hollow fibers from the vessel and replace them with fresh hollow fibers and inoculate these fibers with fresh cells.

The subject hollow fiber structures and apparatus have utility in culturing a variety of cell lines. These techniques may be applied to the production of pharmaceutical materials, diagnostic materials, reagents and single cell proteins. Other techniques for using these hollow fiber structures to culture cells will be apparent to one of ordinary skill in the art.

The invention will be further clarified by a consideration of the following examples, which are intended to be purely exemplary of the present invention.

EXAMPLE 1

Cellulose acetate hollow fibers obtained from a CD-Medical hemodialyzer (C-DAK TM 4000), the fibers having a molecular weight cutoff of 40,000 daltons and inside diameter of 200 microns) were cut into approximately one-sixteenth inch (approximately 0.16 cm) lengths. The cut fibers were sterilized with ethylene oxide and one gram of the fiber, containing approximately 200 $cm^2$ of surface area, was aseptically added to each of two 250 mL spinner flasks.

The fibers in each flask were prewetted by adding 100 mL of Dulbecco's Modification of Eagle's Medium (DMEM) containing 10% fetal bovine serum and mixed in a 37° C., 5% $CO_2$ environment until the medium was equilibrated. Each flask was then inoculated with $1.5 \times 10^7$ VERO cells (African Green Monkey Kidney Cells. ATCC CCL 81) obtained from T-flasks or roller bottles. The separate spinner flasks were placed on a magnetic stirrer and stirred continuously at 60 rpm for the duration of the trial. The cells were cultured at 37° C., under an atmosphere of 5% $CO_2$ and 95% air.

The number of cells in each flask at various time intervals was measured by a fluorescence cell assay performed as follows: Thirty fibers were aseptically removed from each flask and placed into centrifuge tubes and washed with 1.0 mL of washing buffer (150 mM NaCl, 15 mM citrate, 3 mM ethylenediaminetetraacetic acid (EDTA), pH 7.0). The tubes were centrifuged for 15-20 seconds at $13,600 \times G$, the supernatant removed and the pellet resuspended in 50 $\mu L$ of AT extraction solution (1.0N $NH_4OH$, 0.2% Triton X-100). The suspension was then sonicated for approximately 45 seconds, the tubes capped and then incubated for 20 minutes at 37° C. The suspension was then diluted with 1.0 mL of assay buffer (100 mL NaCl, 10 mM EDTA, 10 mM tris[hydroxymethyl]aminomethane, pH 7.0), the tubes centrifuged for 10 minutes at $13,600 \times G$ and the supernatant removed. Fifty microliters of each supernatant were then placed in separate test tubes and 1.5 mL of Hoechst solution (bisbenzimide diluted in assay buffer to give 100 ng/mL) added to each tube. The fluorescence of each tube was then measured with a spectrofluorometer using an excitation wavelength of 350 nm and an emission wavelength of 455 nm.

The average number of cells per flask at various time intervals for this trial is given in Table I.

TABLE I

| Number of VERO cells per flask | |
|---|---|
| Time from inoculation (hours) | Cell number |
| 4 | $1.17 \times 10^6$ |
| 10 | $7.00 \times 10^6$ |
| 21 | $2.45 \times 10^7$ |
| 46 | $6.18 \times 17^6$ |
| 75 | $1.35 \times 10^8$ |
| 264 | $1.50 \times 10^9$ |

EXAMPLE 2

Polysulfone fibers (Anchornet D having a positive surface charge and Anchornet CM having a negative surface charge) with an inside diameters 600 microns were obtained from Kinetic Systems Inc. hollow fiber bioreactor cartridges. The fibers were cut into approximately one-fourth inch (approximately 0.64 cm) segments and one gram of each fiber type placed separately placed in duplicate into separate 250 mL spinner flasks. The fibers and flasks were then steam sterilized. C-DAK TM cellulose acetate fibers as in Example 1 were cut into approximately one-eighth inch (approximately 0.32 centimeters) segments, sterilized with ethylene oxide and one gram of fiber aseptically transferred to separate spinner flasks.

The fibers were prewetted as in Example 1 and each flask inoculated with $1.0 \times 10^7$ VERO cells. The flasks were stirred at 60 rpm for 72 hours at which time the stir rate was increased to 300 rpm. The cells were cultured at 37° C., under an atmosphere of 5% $CO_2$ and 95% air.

The average number of cells per flask for these fibers at various time intervals as measured by the fluorescence cell assay described in Example 1 is given in Table II.

TABLE II

| Time from inoculation (hours) | Number of VERO cells per flask | | |
|---|---|---|---|
| | Polysulfone D Fibers | Polysulfone CM Fibers | Cellulose Acetate Fibers |
| 24 | $1.60 \times 10^5$ | $6.39 \times 10^6$ | $6.05 \times 10^6$ |
| 48 | $1.35 \times 10^5$ | $1.06 \times 10^7$ | $1.41 \times 10^7$ |
| 72 | $1.38 \times 10^6$ | $3.75 \times 10^7$ | $6.74 \times 10^7$ |
| 96 | $3.73 \times 10^6$ | $1.91 \times 10^7$ | $4.28 \times 10^7$ |
| 144 | $1.87 \times 10^6$ | $4.05 \times 10^7$ | $1.49 \times 10^8$ |
| 168 | $3.87 \times 10^6$ | $4.65 \times 10^7$ | — |
| 216 | — | $7.07 \times 10^7$ | $1.40 \times 10^8$ |
| 240 | — | $3.73 \times 10^7$ | $1.15 \times 10^8$ |
| 264 | — | $3.80 \times 10^7$ | $3.30 \times 10^8$ |
| 336 | — | $1.43 \times 10^8$ | $4.09 \times 10^8$ |
| 340 | — | $1.42 \times 10^8$ | $2.45 \times 10^8$ |
| 456 | — | $1.26 \times 10^8$ | $3.01 \times 10^8$ |

EXAMPLE 3

The following fibers cut into one-sixteenth inch (approximately 0.16 cm) segments were tested for supporting cell growth: (1) cellulose triacetate ultrafiltration fiber (CTA-UF, inside diameter 180 microns); and (2) cellulose triacetate microfiltration fiber (CTA-MF, inside diameter 240 microns) obtained from Nipro hemodialyzer and plasma separator cartridges.

One gram of each fiber type was placed in duplicate into separate 250 mL spinner flasks, steam sterilized, prewetted as described in Example 1, and inoculated with $1 \times 10^7$ VERO cells per flask. The flasks were stirred at 60 rpm for 24 hours at which time the stir rate was increased to 300 rpm. The cells were cultured at 37° C., under an atmosphere of 5% $CO_2$ and 95% air.

The average number of cells per flask for these fibers at various time intervals as measured by the fluorescence cell assay described in Example 1 is given in Table III.

TABLE III

| Time from inoculation (hours) | Number of VERO cells per flask | |
|---|---|---|
| | CTA-UF Fibers | CTA-MF Fibers |
| 24 | $1.32 \times 10^7$ | $7.16 \times 10^6$ |
| 48 | $2.51 \times 10^7$ | $2.48 \times 10^6$ |
| 96 | $6.32 \times 10^7$ | $4.81 \times 10^7$ |
| 144 | $8.82 \times 10^7$ | $1.18 \times 10^8$ |
| 312 | $2.02 \times 10^8$ | $1.14 \times 10^9$ |
| 360 | $2.01 \times 10^8$ | $4.22 \times 10^9$ |
| 456 | $3.89 \times 10^8$ | $4.40 \times 10^9$ |
| 624 | $4.26 \times 10^8$ | $1.07 \times 10^9$ |
| 768 | $1.93 \times 10^8$ | $4.15 \times 10^9$ |

EXAMPLE 4

Fibers coated on the lumen surfaces to promote cell adhesion were prepared by coating the lumen surface of soaponified cellulose ester fibers with gelatin. A saponified cellulose ester dialysis hollow fiber dializer (135 SCE) was obtained from CD-Medical. The dialyzer was flushed with 1.0 L of deionized water through the lumen side of the device at 300 mL/min, then rinsed with an additional 2 L of water at 200 mL/min with a transmembrane pressure (TMF) of 250 mm Hg to simultaneously ultrafilter approximately 10 mL/min through the shell side of the device.

A 5,000 parts per million solution of gelatin was prepared by dissolving 4.0 g gelatin (Sigma Chemical Co.) in 800 mL deionized water. The gelatin solution was recirculated through the lumen side of the dialyzer at 150 mL/min for 30 minutes and maintaining a TMP of 250 mm Hg and an ultrafiltration rate of approximately 10 mL/min. The lumen of the device was then drained and the remaining liquid was blown out of the lumen with a 15 second nitrogen sweep and the ends of the lumen then capped off.

A 5% by weight solution of gluteraldehyde was then recirculated through the shell side of the device for one hour. The entire device was then rinsed with 5 liters of deionized water and held overnight to equilibrate any residual gluteraldehyde into the liquid phase. The device was then rinsed with 3 additional liters of water. Subsequently the fibers were cut into approximately one-sixteenth inch (approximately 0.16 cm) segments.

Duplicate one gram samples of the cut fibers were then placed into separate 250 mL spinner flasks and steam sterilized. The fibers were prewetted as in Example 1 and inoculated with $1.5 \times 10^7$ VERO cells. The spinner flasks were placed on a magnetic stirrer and stirred continuously at 60 rpm for the duration of the trial. The cells were cultured at 37° C., under an atmosphere of 5% $CO_2$ and 95% air.

The number of cells per flask at various time intervals, as measured by the fluorescence cell assay described in Example 1. is given in Table IV.

TABLE IV

| Time from inoculation (hours) | Number of VERO cells per flask |
|---|---|
| | Cross Linked Gelatin Coated Saponified Cellulose Ester Fibers |
| 4 | $3.50 \times 10^6$ |
| 10 | $1.40 \times 10^7$ |
| 21 | $1.94 \times 10^7$ |
| 46 | $7.35 \times 10^7$ |
| 75 | $2.17 \times 10^8$ |
| 264 | $7.07 \times 10^8$ |

EXAMPLE 5

Fibers coated on the external surface to prevent cell attachment were prepared by treating the external side of cellulose acetate hollow fibers in a hollow fiber membrane dialysis module obtained from CD Medical, Inc. (C-DAK TM 4000) with a solution containing 250 parts per million (ppm) of a copolymer of methacrylic acid containing 50 mole percent hydroxyethyl methacrylate in distilled water. The treating solution was maintained at a pH of 7.5. The lumen side access ports of the hollow fiber module were sealed with caps and the treating solution applied to the external side of the fiber at ambient pressure and 25° C. During the treating period there was no noticeable permeate flow. Approximately 2 liters of the treating solution were continuously recirculated through the shell side of the module for a 24 hour period. After this period, the module was rinsed twice by filling the shell side of the hollow fiber module with deionized water and emptying. The fibers were removed from the cartridge and cut into ¼ inch (0.63 centimeter) lengths and sterilized with ethylene oxide.

Cellulose acetate hollow fibers cut into approximately ¼ inch (approximately 0.63 centimeter) lengths which were not treated served as controls. One gram of each fiber type, i.e., coated and uncoated controls were aseptically added to respective spinner flasks. The fibers in each flask were prewetted by adding 100 mL of Eagles minimum essential medium (pH 7.2-7.6) and mixed in a 37° C., 5% $CO_2$ environment until the medium was equilibrated. Each flask was then inoculated with $2 \times 10^7$ BSC-1 cells (African Green Monkey Kidney Cells, ATCC CCL 26) obtained from T-flasks or roller bottles. The separate spinner flasks were placed on a magnetic stirrer and stirred continuously at 40-60 rpm for 12 hours to allow attachment of the cells to the fibers. After the initial 12 hour inoculation period, the stirring rate of the vessels was increased to between 250-300 rpm.

To determine the number of cells attached within the lumen of the fibers, thirty fibers were removed from each flask at various time intervals and placed in centrifuge tubes. The fibers were washed with phosphate buffered saline (PBS), pH 7.2, treated 3-5 minutes with a trypsin-EDTA solution, the excess trypsin was removed and the fibers incubated for 15 minutes at 37° C. After 15 minutes, 1 mL of Eagles minimum essential medium was added to inactivate the trypsin. The fibers were then washed with PBS to remove cells dislodged by the trypsin-EDTA treatment. This treatment removes substantially all cells that may have attached to the external surface of the fibers while the cells within the lumen of the fiber remain due to capillary action. The cells retained within the lumen of the fibers were removed by placing the fibers vertically in a centrifuge tube containing a small screen near the bottom which allows cells to pass through but retains the fibers and centrifuging for 2-3 minutes. The cells were then resuspended in cell culture medium and counted on a hemacytometer. The number of cells substantially within the lumen of the fiber segments sampled at various time intervals is given in Table V.

TABLE V

| Time from inoculation (hours) | Number of BSC-1 cells per flask | |
|---|---|---|
| | Coated Fibers | Noncoated Fibers |
| 6 | $4.0 \times 10^5$ | $0.6 \times 10^5$ |
| 12 | $9.1 \times 10^5$ | $2.6 \times 10^5$ |
| 24 | $9.2 \times 10^5$ | $4.3 \times 10^5$ |
| 48 | $1.1 \times 10^6$ | $4.5 \times 10^5$ |
| 96 | $2.1 \times 10^6$ | $6.2 \times 10^5$ |
| 144 | $4.1 \times 10^6$ | $1.1 \times 10^6$ |

It is apparent from the data in Table I that the number of cells recoverable from the exterior surface coated fibers is significantly greater than for the control fibers.

EXAMPLE 6

To determine the effect that a smaller inoculum size would have on cell attachment and growth within the lumen of treated and untreated hollow fibers, fibers and flasks were prepared in duplicate as described in Example 5. After the flasks are equilibrated with the 5% $CO_2$, 37° C. environment, $8.5 \times 10^6$ BSC-1 cells were added to each flask. The spinner flasks were then placed on a magnetic stirrer and the culture mixed at 40 rpm for 52 hours. The medium was then aseptically changed and the stirring rate increased to 250 rpm Samples were taken at various time points and the total cells growing within the lumen of the porous hollow fibers determined as described in Example 5. The total cells per flask growing within the lumen of the control, i.e., untreated fibers, as wells as surface coated fibers, is given in Table VI.

TABLE VI

| Time from inoculation (hours) | Number of BSC-1 cells per flask | |
|---|---|---|
| | Coated Fibers | Noncoated Fibers |
| 6 | $1.0 \times 10^5$ | $1.0 \times 10^5$ |
| 12 | $3.5 \times 10^5$ | $2.1 \times 10^5$ |
| 24 | $8.2 \times 10^5$ | $2.6 \times 10^5$ |
| 52 | $9.9 \times 10^5$ | $2.8 \times 10^5$ |
| 96 | $1.44 \times 10^6$ | $2.0 \times 10^5$ |
| 144 | $1.85 \times 10^6$ | $1.4 \times 10^5$ |

The data shows that during the low agitation, inoculation phase, there is greater attachment and growth of cells within the lumen of the fibers which have been surface coated than for the control fibers. When the agitation rate is increased, the cells within the lumen of the surface coated fibers continue to increase in numbers.

Other embodiments of the invention will be apparent to those skilled in the art from a consideration of this specification or practice of the invention disclosed herein. It is intended that the specification and examples be considered as exemplary only, with the true scope and spirit of the invention indicated by the following claims.

What is claimed is:

1. A method for culturing mammalian cells comprising
   (a) providing a plurality of essentially individual hollow fiber segments in a vessel, the segments each having an exterior surface and an interior surface, wherein each segment comprises a cylindrical wall surrounding a lumen open at at least one end of the fiber, the lumen diameter being in the range from 50 to 1000 microns, and the wall of the hollow fiber segments surrounding the lumen being compatible with retention, growth and propagation of mammalian cells, and the length of the fiber along the axis parallel to the lumen being not more than about 5 centimeters;
   (b) introducing into the vessel a liquid nutrient medium;
   (c) introducing into the vessel a cell culture of anchorage dependent mammalian cells in the presence of the liquid nutrient medium;
   (d) agitating the nutrient medium to distribute the hollow fibers segments in the medium; and
   (e) maintaining conditions in the liquid medium so that the mammalian cells in the cell culture will propagate in the lumen of the individual hollow fiber segments.

2. The method of claim 1 wherein the lumen is open at two opposed ends of a majority of the hollow fibers and a majority of the fibers have a length in the range from about 0.01 centimeter to about 3 centimeters.

3. The method of claim 2 wherein the fiber wall consists predominantly of a polymer selected from the group consisting of a cellulose ester, polyvinylalcohol, polyamide, polyvinly chloride, an organic silicone polymer, polyacrylonitrile, a copolymer of styrene and acrylonitrile, polysulfone, polyethersulfone, polyesters, polycarbonate, and polymethylmethacrylate.

4. The method of claim 3 wherein the fiber walls are porous.

5. The method of claim 2 wherein the mammalian cells are selected from the group consisting of Chinese hamster ovary, human lung fibroblast, or fetal human lung fibroblast, African green monkey kidney, foreskin fibroblast and Hela human cervix cell line.

6. The method of claim 2 wherein the fiber segments are essentially free of cell lines other than the one to be cultured when the cells to be cultured and fiber segments are brought together in the vessel.

7. The method of claim 1 wherein agitation of the nutrient medium produces a shear stress sufficiently high to damage or dislodge cells present on the outer surface of the hollow fiber segments.

8. The method of claim 1 wherein the fiber segments are treated or modified with a material to promote cell adhesion.

9. The method of claim 8 wherein the fiber wall consists predominantly of a polymer selected from the group consisting of a cellulose ester, polyvinylalcohol, polyamide, polyvinly chloride, an organic silicone polymer, polyacrylonitrile, a copolymer of styrene and acrylonitrile, polysulfone, polyethersulfone, polyesters, polycarbonate, polymethylmethacrylate, polystyrene, polypropylene, polyethylene, polymethylpentene and a saponified cellulose ester.

10. The method of claim 8 wherein the lumen of the fiber segments is coated with a material selected from the group consisting of collagen, fibronectin, polylysine, gelatin and an adhesion peptide.

11. The method of claim 1 wherein the lumen diameter is in the range of from about 50 to about 600 microns.

12. A method for culturing mammalian cells comprising
(a) providing a plurality of essentially individual hollow fiber segments in a vessel, the segments each having an exterior surface and an interior surface, wherein each segment comprises a cylindrical wall surrounding a lumen open at at least one end of the fiber, the lumen diameter being in the range from 50 to 100 microns, and the wall of the hollow fiber segments surrounding the lumen being compatible with retention, growth and propagation of mammalian cells, and the length of the fiber along the axis parallel to the lumen being not more than about 5 centimeters, and the exterior surfaces of the segments are characterized as substantially preventing attachment and growth of mammalian cells thereon;
(b) introducing into the vessel a liquid nutrient medium;
(c) introducing into the vessel a cell culture of anchorage dependent mammalian cells in the presence of the liquid nutrient medium;
(d) agitating the nutrient medium to distribute the hollow fibers segments in the medium; and;
(e) maintaining conditions in the liquid medium so that the mammalian cells in the cell culture will propagate in the lumen of the individual hollow fiber segments.

13. The method of claim 12 wherein the exterior surface of the hollow fiber segments has been treated with a vinyl addition polymer sufficient to substantially prevent attachment and growth of mammalian cells.

14. The method of claim 13 wherein the lumen is open at two opposed ends of a majority of the hollow fibers and a majority of the fibers have a length in the range from about 0.01 centimeter to about 3 centimeters.

15. The method of claim 13 wherein the fiber wall consists predominantly of a polymer selected from the group consisting of a cellulose ester, polyvinylalcohol, a polyamide, polyvinly chloride, an organic silicone polymer, polyacrylonitrile, a copolymer of styrene and acrylonitrile, polysulfone, polyesters, polyethersulfone, polycarbonate, and polymethylmethacrylate.

16. The method of claim 15 wherein the fiber walls are porous.

17. The method of claim 13 wherein the vinyl addition polymer is comprised of hydroxyethyl methacrylate and methacrylic acid.

18. The method of claim 13 wherein the mammalian cells are selected from the group consisting of Chinese hamster ovary, human lung fibroblast, fetal human lung fibroblasts, African green monkey kidney, foreskin fibroblast and Hela human cervix cell line.

19. The method of 13 wherein the fiber segments are essentially free of cell lines other than the one to be cultured when the cells to be cultures and fiber segments are brought together in the vessel.

20. The method of claim 12 wherein the lumen of the fiber segments has been coated with a material to promote cell adhesion.

21. The method of claim 20 wherein the fiber wall consists predominantly of a polymer selected from the group consisting of a cellulose ester, polyvinylalcohol, a polyamide, polyvinyl chloride, an organic silicone polymer, polyacrylonitrile, a copolymer of styrene and acrylonitrile, polysulfone, polyesters, polyethersulfone, polycarbonate, polymethylmethacrylate, polystyrene, polypropylene, polyethylene, polymethylpentene and a saponified cellulose ester.

22. The method of claim 20 wherein the lumen of the fiber segments is coated with a material selected from the group consisting of collagen, fibronectin, polylysine, gelatin and an adhesion peptide.

23. A method for culturing mammalian cells comprising
(a) providing a plurality of essentially individual hollow fiber segments in a vessel, the segments each having an exterior surface and an interior surface, wherein each segment comprises a cylindrical wall surrounding a lumen open at at least one end of the fiber, the lumen diameter being in the range from 50 to 1000 microns, and the wall of the hollow fiber segment surrounding the lumen being compatible with retention, growth and propagation of mammalian cells, and the length of the fiber along the axis parallel to the lumen being not more than about 5 centimeters, and, the exterior surfaces of the segments are characterized as substantially preventing attachment and growth of mammalian cells thereon;
(b) introducing into the vessel a liquid nutrient medium;
(c) introducing into the vessel a cell culture of adherent hybridoma mammalian cells in the presence of the liquid nutrient medium;
(d) agitating the nutrient medium to distribute the hollow fibers segments in the medium; and
(e) maintaining conditions in the liquid medium so that the hybridoma mammalian cells in the cell culture will propagate in the lumen of the individual hollow fiber segments.

24. The method of claim 23 wherein the lumen of the fiber segments is treated or modified with a material to promote cell adhesion.

25. The method of claim 24 wherein the exterior surfaces of the segments are characterized as substantially preventing attachment and growth of mammalian cells thereon.

* * * * *